United States Patent
Nicholls et al.

(10) Patent No.: US 9,066,699 B2
(45) Date of Patent: Jun. 30, 2015

(54) LANCING DEVICES

(71) Applicant: OWEN MUMFORD LIMITED, Oxford (GB)

(72) Inventors: Clive Nicholls, Buckinghamshire (GB); Robert Michael Wozencroft, Surrey (GB)

(73) Assignee: OWEN MUMFORD LIMTED, Oxford (GB)

( * ) Notice: Subject to any disclaimer, the term of this patent is extended or adjusted under 35 U.S.C. 154(b) by 0 days.

(21) Appl. No.: 14/150,111

(22) Filed: Jan. 8, 2014

(65) Prior Publication Data

US 2014/0121693 A1 May 1, 2014

Related U.S. Application Data

(62) Division of application No. 12/673,260, filed on Jun. 1, 2010, now Pat. No. 8,663,265.

(30) Foreign Application Priority Data

Aug. 14, 2007 (GB) .................................. 0715801.7

(51) Int. Cl.
*A61B 5/151* (2006.01)
*A61B 5/15* (2006.01)

(52) U.S. Cl.
CPC ............. *A61B 5/15144* (2013.01); *A61B 5/151* (2013.01); *A61B 5/1519* (2013.01); *A61B 5/150175* (2013.01); *A61B 5/15188* (2013.01); *A61B 5/150022* (2013.01); *A61B 5/15107* (2013.01); *A61B 5/15113* (2013.01); *A61B 5/150183* (2013.01); *A61B 5/1411* (2013.01); *A61B 5/15186* (2013.01)

(58) Field of Classification Search
CPC ............. A61B 5/1411; A61B 5/15146; A61B 5/15186; A61B 5/15188; A61B 5/1519; A61B 5/15192; A61B 5/15194; A61B 5/150022; A61B 5/150175; A61B 5/150183; A61B 5/15019; A61B 5/150198
USPC .......... 606/181–185, 167, 117; 600/573, 583; 604/131, 134

See application file for complete search history.

(56) References Cited

U.S. PATENT DOCUMENTS

| | | | |
|---|---|---|---|
| 5,318,584 A | 6/1994 | Lange et al. | |
| 5,613,978 A | * 3/1997 | Harding | ........................ 606/181 |
| 5,797,942 A | 8/1998 | Schraga | |
| 6,346,114 B1 | 2/2002 | Schraga | |
| 6,530,937 B1 | 3/2003 | Schraga | |
| 2002/0040230 A1 | 4/2002 | Kuhr | |

(Continued)

FOREIGN PATENT DOCUMENTS

EP 1 625 824 A 2/2006

*Primary Examiner* — Ryan Severson
*Assistant Examiner* — Rachel S Papeika
(74) *Attorney, Agent, or Firm* — Young & Thompson (57) ABSTRACT

A lancing device includes a housing (10, 12) for receiving in use a replaceable lancet (34) introduced into said housing, a drive (58, 59) actuable to drive the lancet momentarily to project its tip from the housing, and a nose portion (14) having an aperture through which said lancet projects when fired. The nose portion is threadedly engaged (78, 81) with the forward end (10) of the housing to allow the penetration depth of said lancet tip to be pre-set, and is resiliently deformable between a position in which it is locked against rotation and a position in which it is free to rotate.

20 Claims, 10 Drawing Sheets

(56) References Cited

U.S. PATENT DOCUMENTS

| | | |
|---|---|---|
| 2002/0082633 A1 | 6/2002 | Schraga |
| 2002/0162817 A1 | 11/2002 | Vassallo |
| 2003/0187470 A1 | 10/2003 | Chelak et al. |
| 2004/0034318 A1* | 2/2004 | Fritz et al. .................. 604/19 |
| 2004/0092996 A1 | 5/2004 | List et al. |
| 2004/0222181 A1 | 11/2004 | Biesecker et al. |
| 2004/0254599 A1 | 12/2004 | Lipoma et al. |
| 2005/0090850 A1 | 4/2005 | Thoes et al. |
| 2005/0159768 A1 | 7/2005 | Boehm et al. |
| 2005/0234492 A1* | 10/2005 | Tsai et al. ................... 606/181 |
| 2007/0173876 A1* | 7/2007 | Aylett et al. ................. 606/181 |

* cited by examiner

LANCING DEVICES

BACKGROUND OF THE INVENTION

1. Field of the Invention

This invention relates to lancing devices and in particular, but not exclusively, to such lancing devices for use with a replaceable lancet.

2. Description of the Related Art

There is a need for lancing devices in which a disposable lancet is introduced into the device and released therefrom with the minimum of handling.

SUMMARY OF THE INVENTION

Accordingly, in one aspect, this invention provides a lancing device comprising a housing, a lancet holder within the housing for receiving in use a replaceable elongate lancet introduced into said housing, a drive actuable to drive said lancet momentarily to project a tip from the housing, a lancet release element for effecting relative angular movement of said lancet holder and said lancet generally about the longitudinal axis of the lancet from a position in which said lancet is retained by said holder and a position in which said lancet is released from said retention.

Although we do not exclude the possibility of the lancet being rotatable about its longitudinal axis, it is preferred for said lancet holder to be rotatable with respect to said housing.

Where said lancet has a main body portion of non-circular cross-section, said housing preferably has a non-circular cross-section passage of similar shape through which said lancet is introduced into said housing.

Advantageously, said lancet holder is adapted to receive said lancet in snap engagement when the latter is pushed into said device.

Preferably said lancet holder is slideably and non-rotatably engaged with said lancet release, said release element being rotatably disposed within the housing and having an externally accessible portion.

Said drive mechanism conveniently includes a hammer moveable to a cocked position within said housing, with said lancet release element preferably being adapted to latch said hammer in its cocked position.

In one arrangement the device includes a rotatable nose portion having an aperture through which said lancet projects when fired, said nose portion being threadedly engaged with the forward end of said housing to allow the penetration depth of said lancet tip to be pre-set. Said nose portion may have a generally cylindrical rearward skirt having abutments disposed to face complementary abutments on or associated with said housing, said skirt portion being resiliently deformable between a position in which said abutments engage to prevent or resist rotary movement of said nose portion, and a position in which said abutment means move away from each other to allow rotation.

In another arrangement, the device includes a nose portion assembly mounted on the forward end of said housing, said nose portion assembly comprising a non-rotatable nose portion element slideably and non-rotatably mounted on the forward end of said housing, the nose portion being captive on a rotary collar which is threadedly engaged with the forward end portion of the housing to allow the penetration depth of the lancing device to be pre-set.

In another aspect this invention provides a lancing device comprising a housing for receiving in use a replaceable lancet introduced into said housing, drive means actuable to drive said lancet momentarily to project its tip from the housing, and a nose portion having an aperture through which said lancet projects when fired, said nose portion being threadedly engaged with the forward end of said housing to allow the penetration depth of said lancet tip to be pre-set, said nose portion being resiliently deformable between a position in which it is locked against rotation and a position in which it is free to rotate.

In yet another aspect this invention provides a lancing device comprising a housing for receiving in use a replaceable lancet introduced into said housing, drive means actuable to drive said lancet momentarily to project its tip from the housing, and a nose portion assembly mounted on the forward end of said housing, said nose portion assembly comprising a nose portion element slideably and non-rotatably mounted on the forward end of said housing, the nose portion being captive on a rotary collar which is threadedly engaged with the forward end portion of the housing to allow the penetration depth of the lancing device to be pre-set.

Whilst the invention has been described above, it extends to any inventive combination or sub-combination of the features set out above or in the following description.

BRIEF DESCRIPTION OF THE DRAWING FIGURES

Two embodiments of the invention will be described by way of example only, reference being made to the accompanying drawings, in which.

DETAILED DESCRIPTION OF THE INVENTION

Referring initially to the first embodiment shown in FIGS. 1 to 9, this comprises forward and rearward housing parts, 10, 12 with a rotary nose portion 14 captive on the forward housing part 10, for penetration depth adjustment. The device is designed to receive a removable lancet (shown in later Figures) which is introduced through the front end of the device and releasably retained therein. Once loaded with a lancet, the device is cocked using a cocking slider 16, fired using a firing button 18, and the lancet then released using a lancet release lever 20.

Referring now more particularly to FIGS. 2 and 4 to 8, the forward housing 10 slideably receives a lancet holder 22 which has a cylindrical rear portion 24 to the forward end of which is a circumferential guide flange 26, and extending forwardly are two resiliently deformable arms 28 terminating forwardly in inwardly directed barbs 30. The lancet holder 22 is urged rearwardly by means of a compression spring 32 acting between the guide flange 26 and a rearwardly facing shoulder in the forward housing part 10. The resiliently deformable arms 28 with their inwardly directed barbs 30 are designed to receive in one way snap engagement the rear end of a lancet 34. The lancet has a main body portion having a central cylindrical stem 36 and diametrically opposed flanges 38. The flanges are chamfered at the rear end to assist engagement and snapping past the resilient barbs 30, and then cut away at 40 to form a latch recess for the inwardly directed barbs. The lancet holder 22 includes a thrust surface 41 against which the rear end of the lancet rests. The cylindrical portion 24 includes two diametrically opposed lugs 42 which fit into respective slots 44 formed in a cylindrical shell portion 46 forming part of the lancet release lever 20. The lancet release lever 20 has protruding flaps 48 which protrude through diametrically opposed slots 50 formed between the forward and rearward housing parts. The lancet release lever 20 is biased in the clockwise direction when viewed from the front by means of a torsion spring 52 engaged at its forward end with the cylindrical shell 46 and at its rearward end on a seat within the rearward housing part 12. The cylindrical portion 24 of the lancet release lever 20 steps in rearwardly to provide an inner cylindrical portion 54, which defines a cylindrical latching surface 56.

A hammer 58 is slideably received in the inner cylindrical portion 54 and urged forwardly by a drive spring 59 acting between the hammer and a rear end of the rearward housing part. The hammer is provided with a forwardly extending resiliently deformable arm 60 having a barb 62 on it for cooperating with the latching surface 56 on the cylindrical portion 54 to latch the hammer in a cocked position. Surrounding the aft end of the hammer is a cylindrical cocking shell 64 having two inwardly directed lugs 66 which project to either side of a longitudinal ventral rib 68 on the hammer 58. At its rearward end the hammer is provided with a rear end disc 70. The cocking slider 16 is connected to the cocking sleeve 64 by a snap fit through a slider slot 72. The slider is biased forwardly by a compression spring 74.

At its front end, the forward housing part has an aperture 74 designed to receive the cross-section of the lancet 34, thus comprising a circular centre with diametrically opposed grooves. The aperture 74 is at the front end of a guide passage 76 of constant cross-section which provides support for the lancet during loading, firing and unloading.

The forward portion of the forward housing part is externally threaded at 78 and, rearwardly thereof on a stepped outwardly portion is a series of locking splines 80. The nose portion 14 has an internal threaded region 81 so that it can be screwed onto the front of the forwarding housing part. The nose portion has a rearward cylindrical skirt 82 designed to fit with clearance over the corresponding surface of the forward housing portion. The skirt has two longitudinal ribs 84 which cooperate with the splines 80, to restrict or prevent rotation of the nose portion when relaxed. At 90° around the circumference of the skirt 82 are two pressure pads 86. The nose portion is designed relative to the forward housing part so that, on pressing the pressure pads 86 towards each other, the locking ribs 84 are lifted away from engagement with the splines so that the nose portion can be rotated to adjust the axial position of its foremost portion and thus the penetration depth. The nose portion 14 has a central, circular aperture through which the tip of the lancet 34 projects momentarily when fired.

Figure 1:
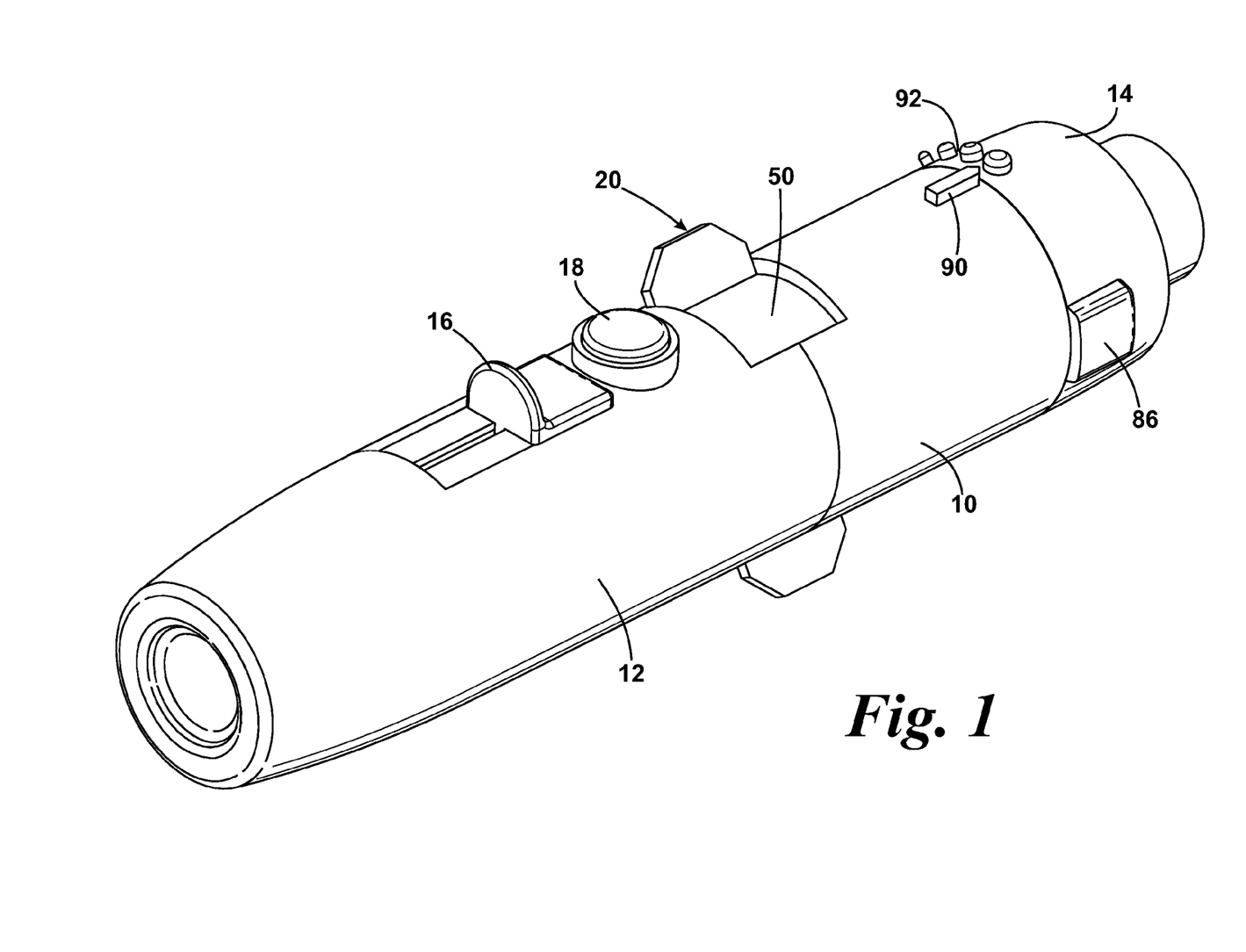
FIG. 1 is a general perspective view of a first embodiment of lancing device in accordance with this invention.
Figure 2:
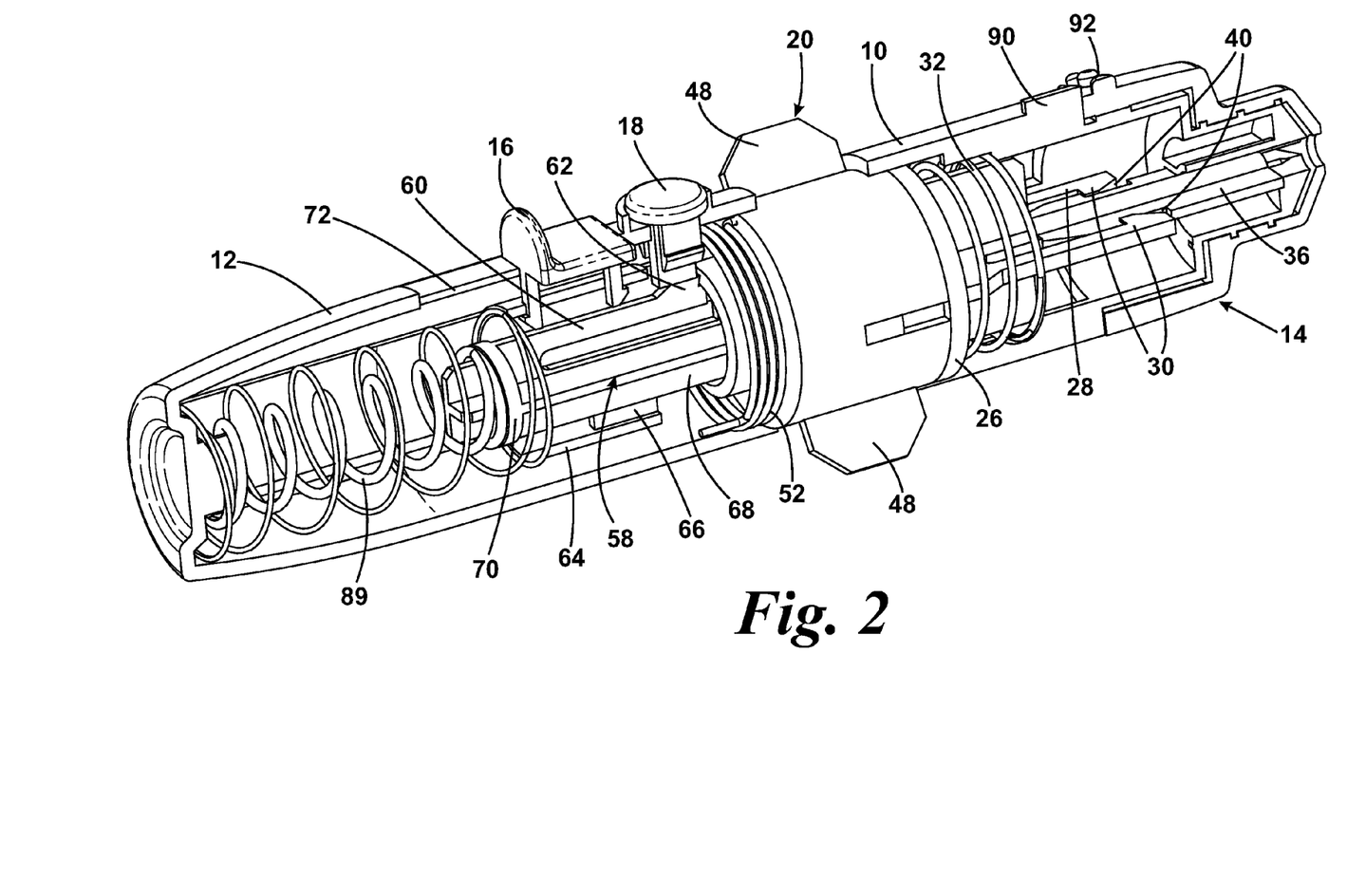
FIG. 2 is a view similar to FIG. 1 but with part of the casing removed, showing the device with a lancet loaded and the hammer cocked.
Figure 3:
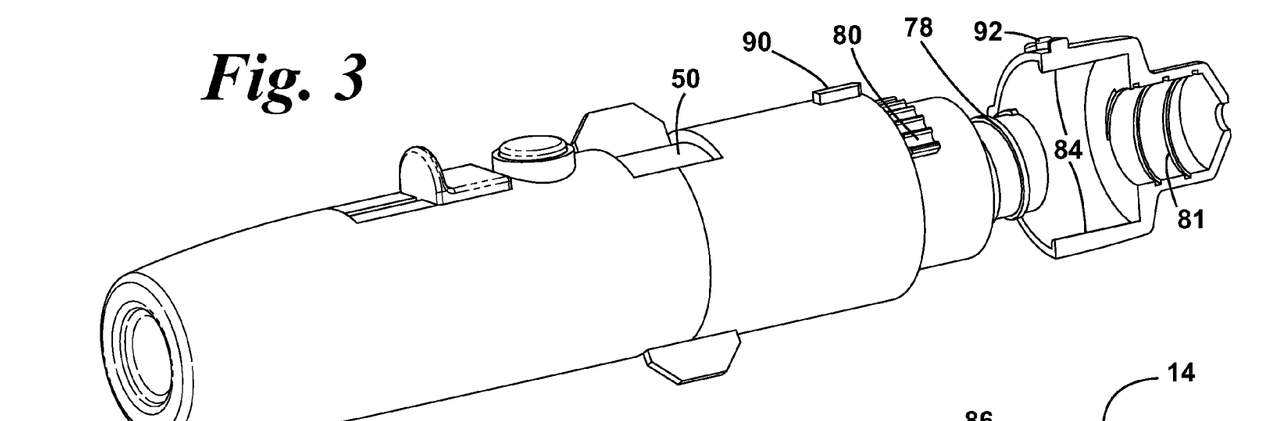
FIG. 3 is a view similar to FIG. 1 but showing the nose piece removed forwardly for introduction/disposal of a lancet.
Figure 4:
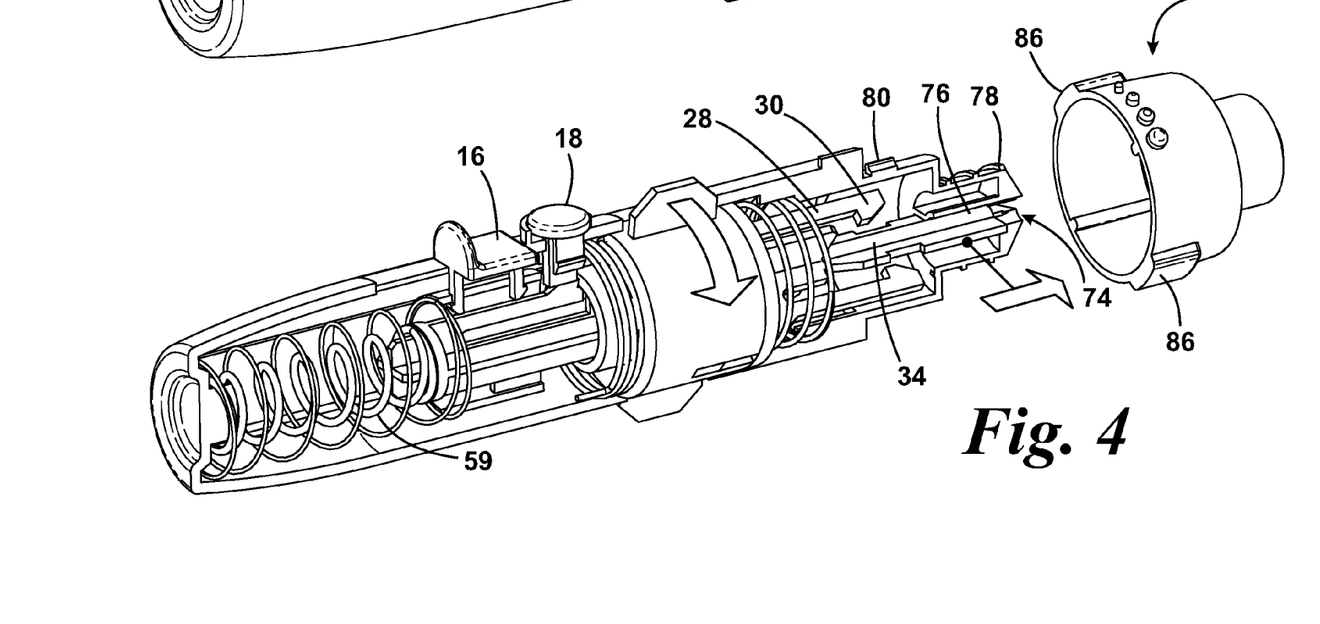
FIG. 4 is a view similar to FIG. 2 with the hammer in a cocked position but showing the lancet holder rotated to release a lancet.
Figure 5:
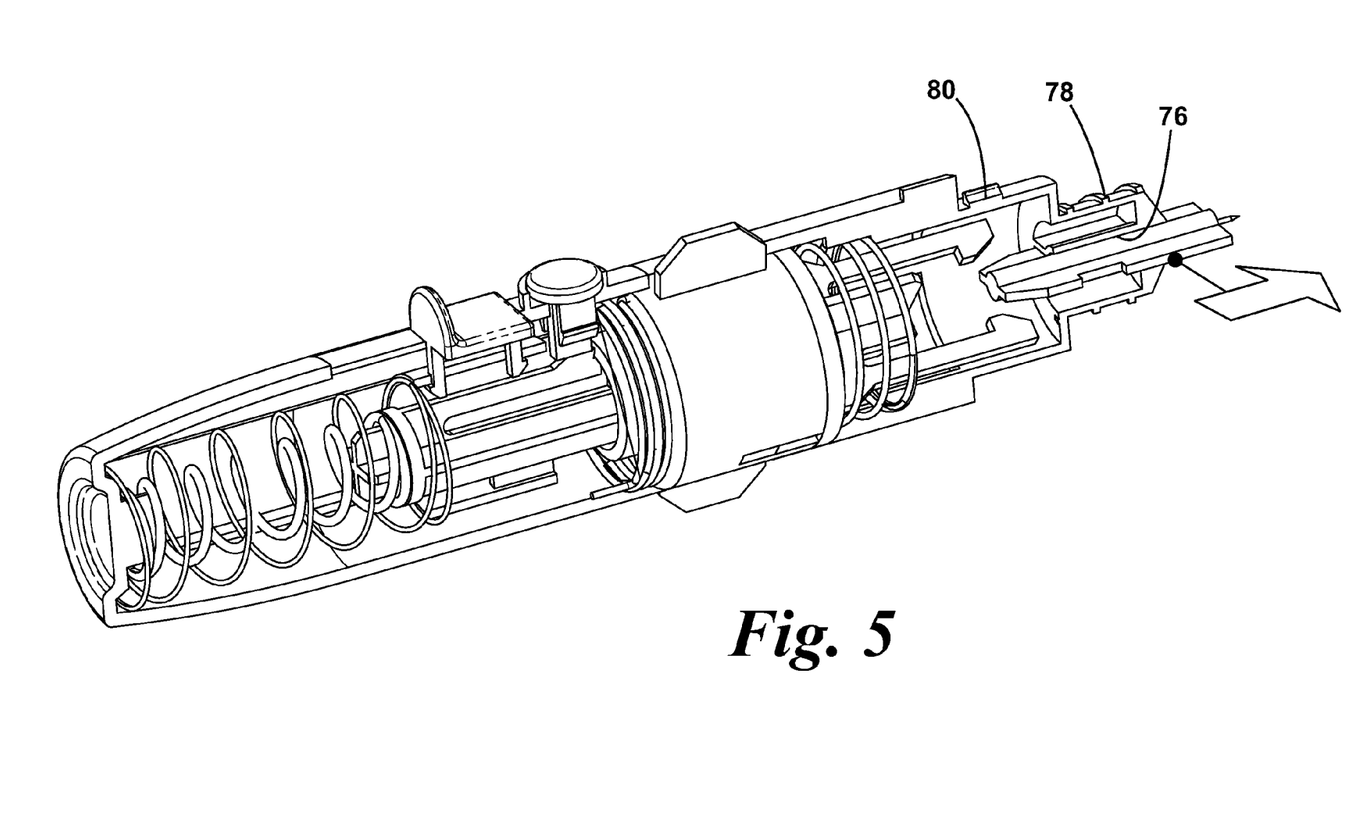
FIG. 5 is a view similar to FIG. 4 but showing the lancet exiting the housing.
Figure 6:
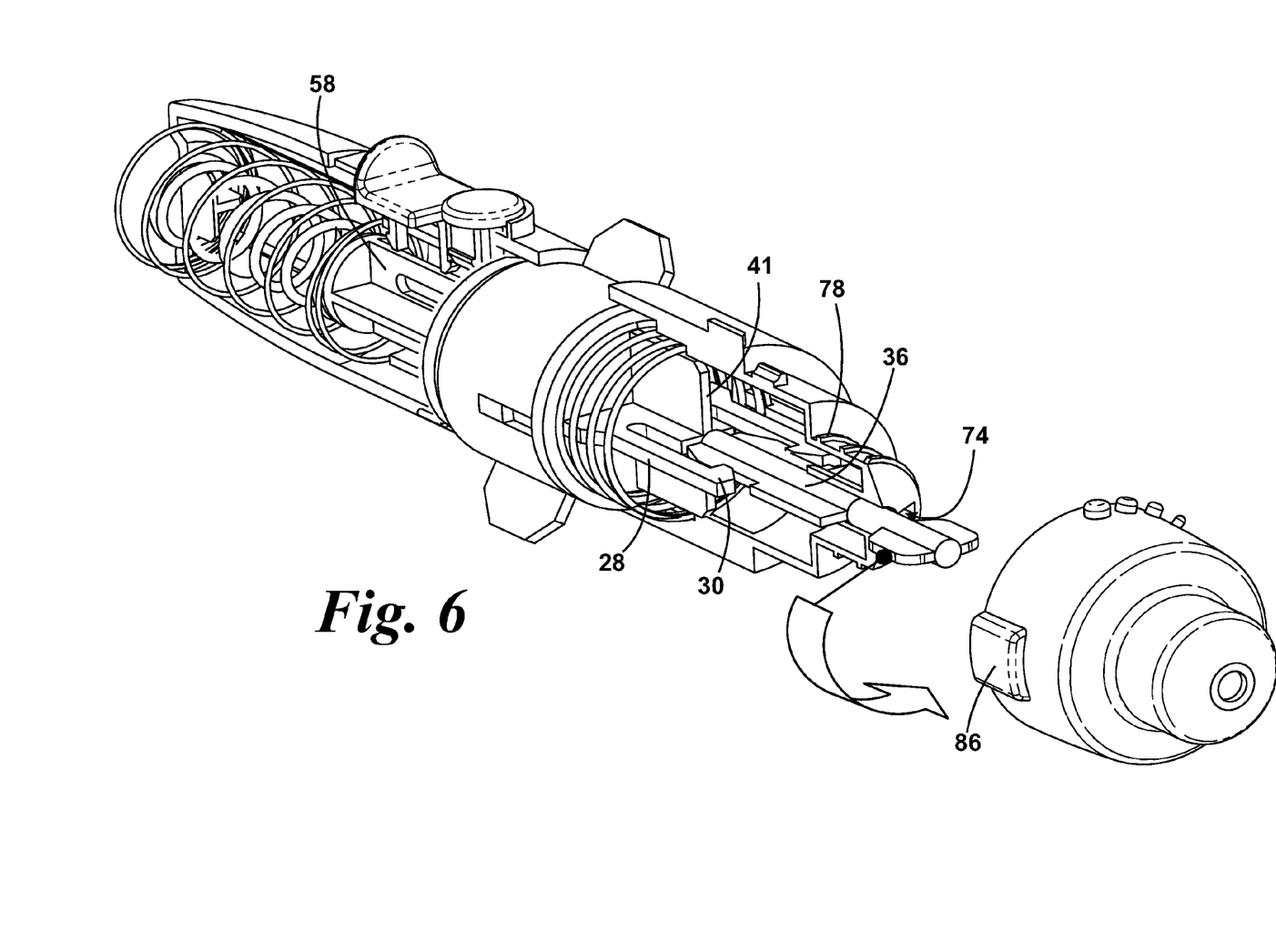
FIG. 6 is a view showing a new lancet pushed into engagement with the lancet holder with the hammer cocked.
Figure 7:
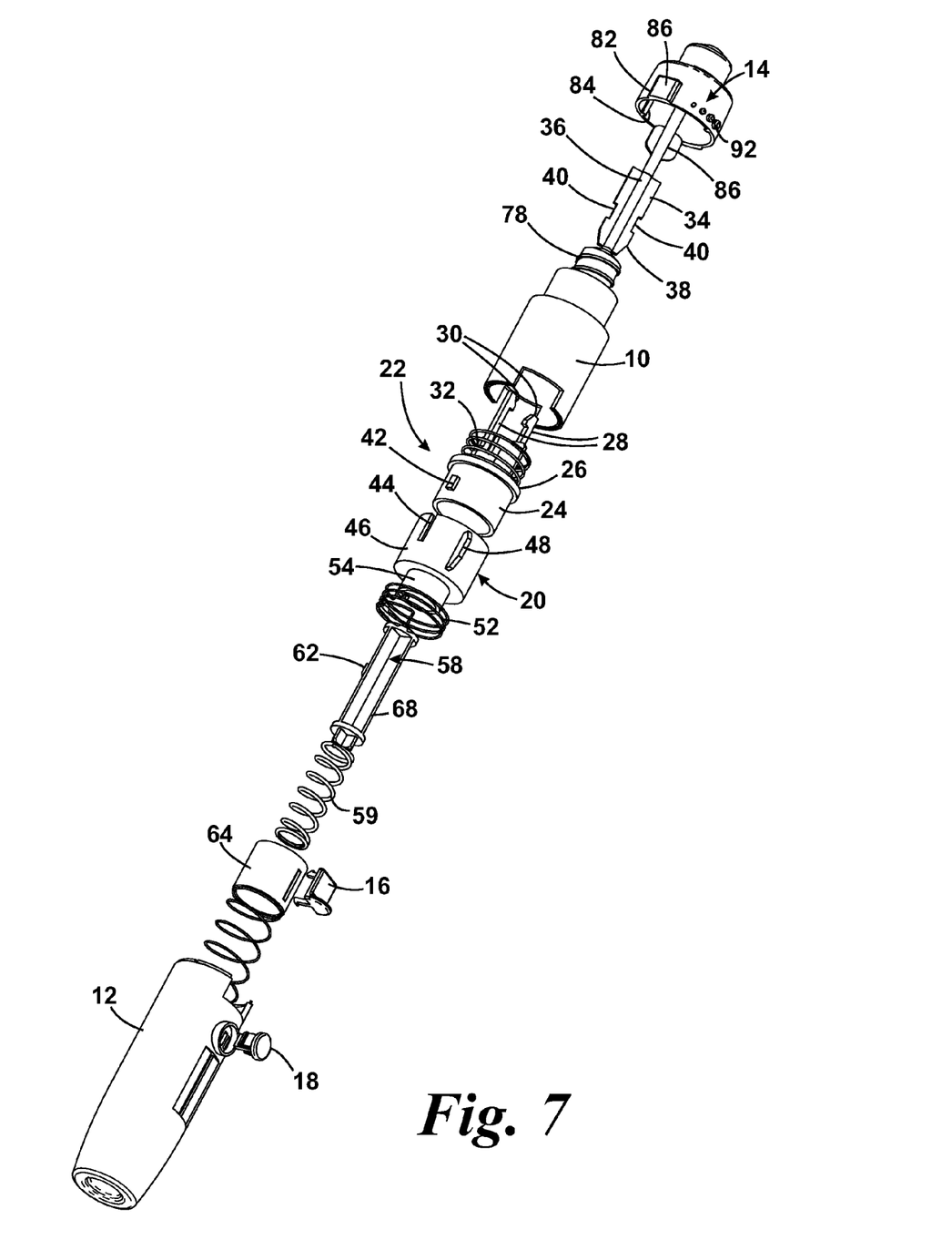
FIG. 7 is an exploded view of the first embodiment of lancing device.
Figure 8:
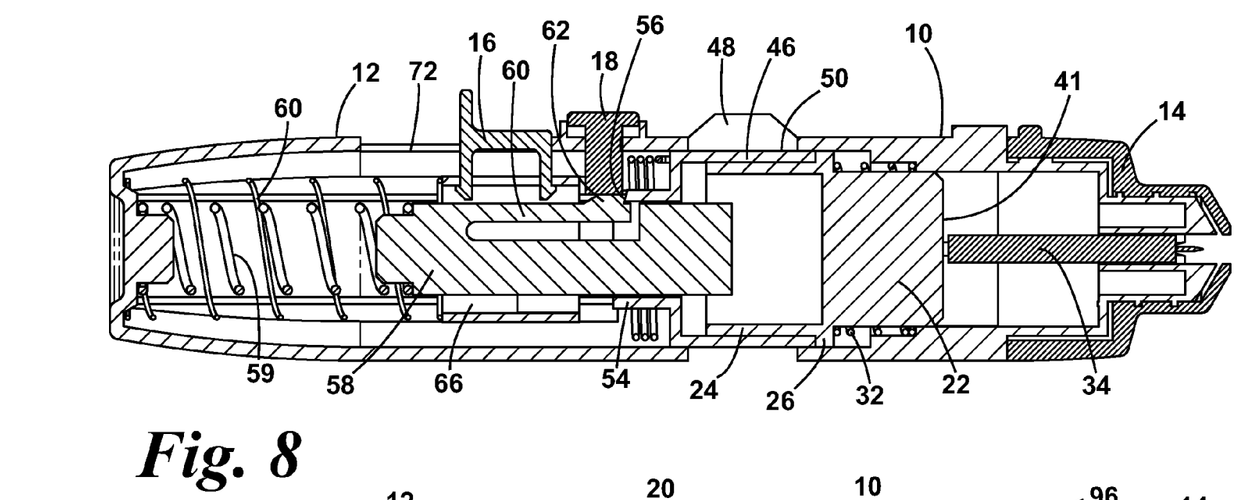
FIG. 8 is a longitudinal sectional view through the first embodiment of lancing device loaded with a lancet and with the hammer cocked.
Figure 9:
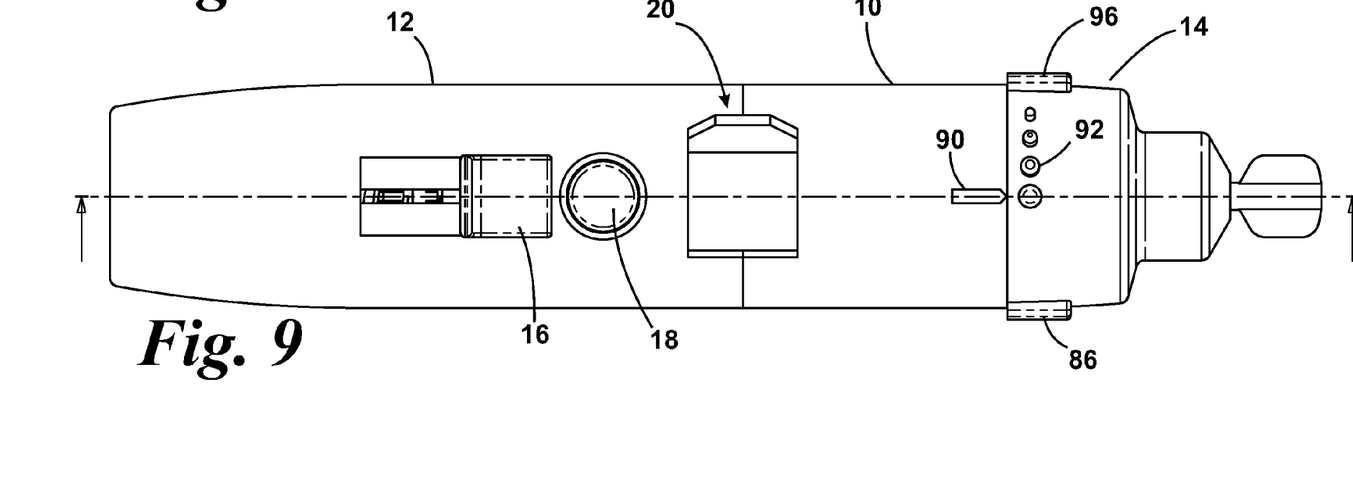
FIG. 9 is a top plan view of the first embodiment of lancing device.
Figures 10, 11:
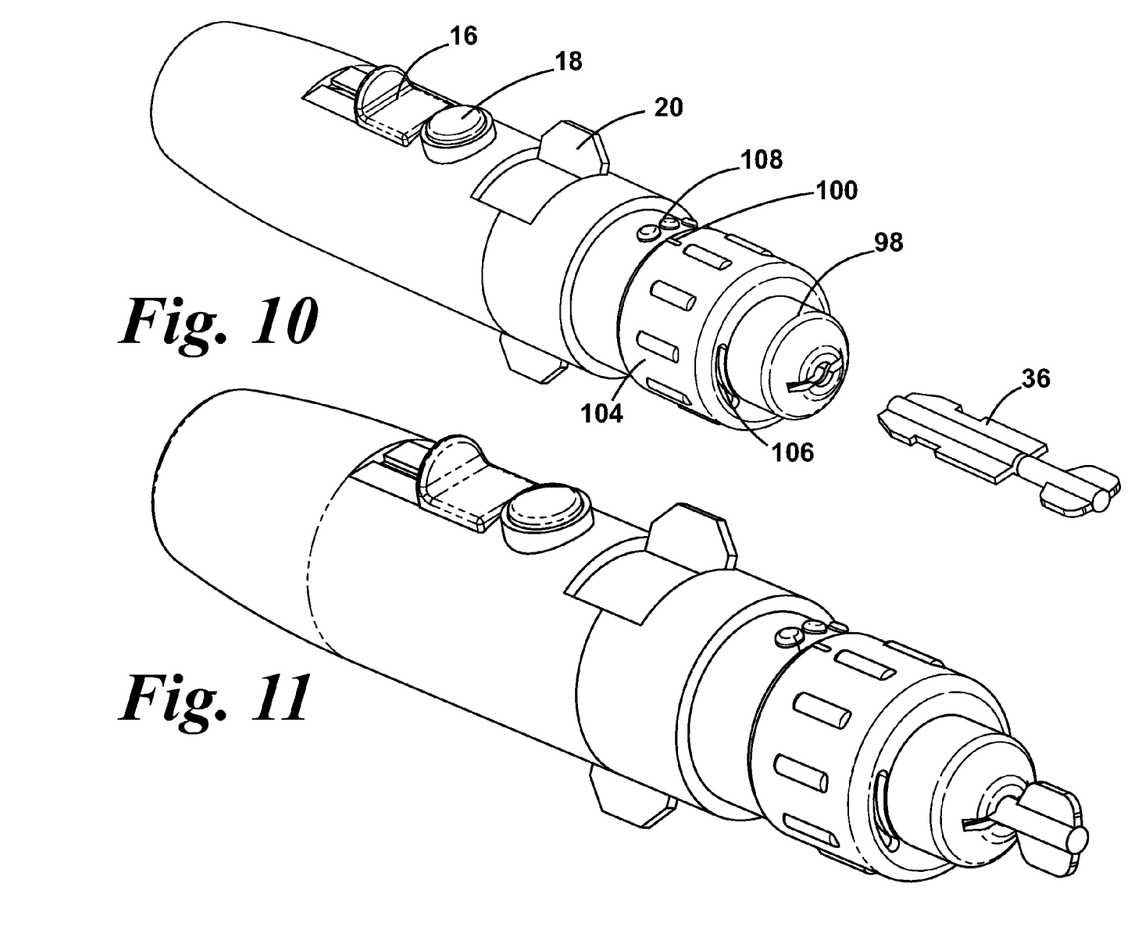
FIG. 10 is a perspective view of a second embodiment of lancing device in accordance with this invention with a modified depth adjustment mechanism which allows the lancet to be loaded without removing the nose portion of the device, and with the lancet about to be inserted into the device.
FIG. 11 is a view similar to FIG. 10 but showing the lancet cap being twisted off.
Figures 12, 13:
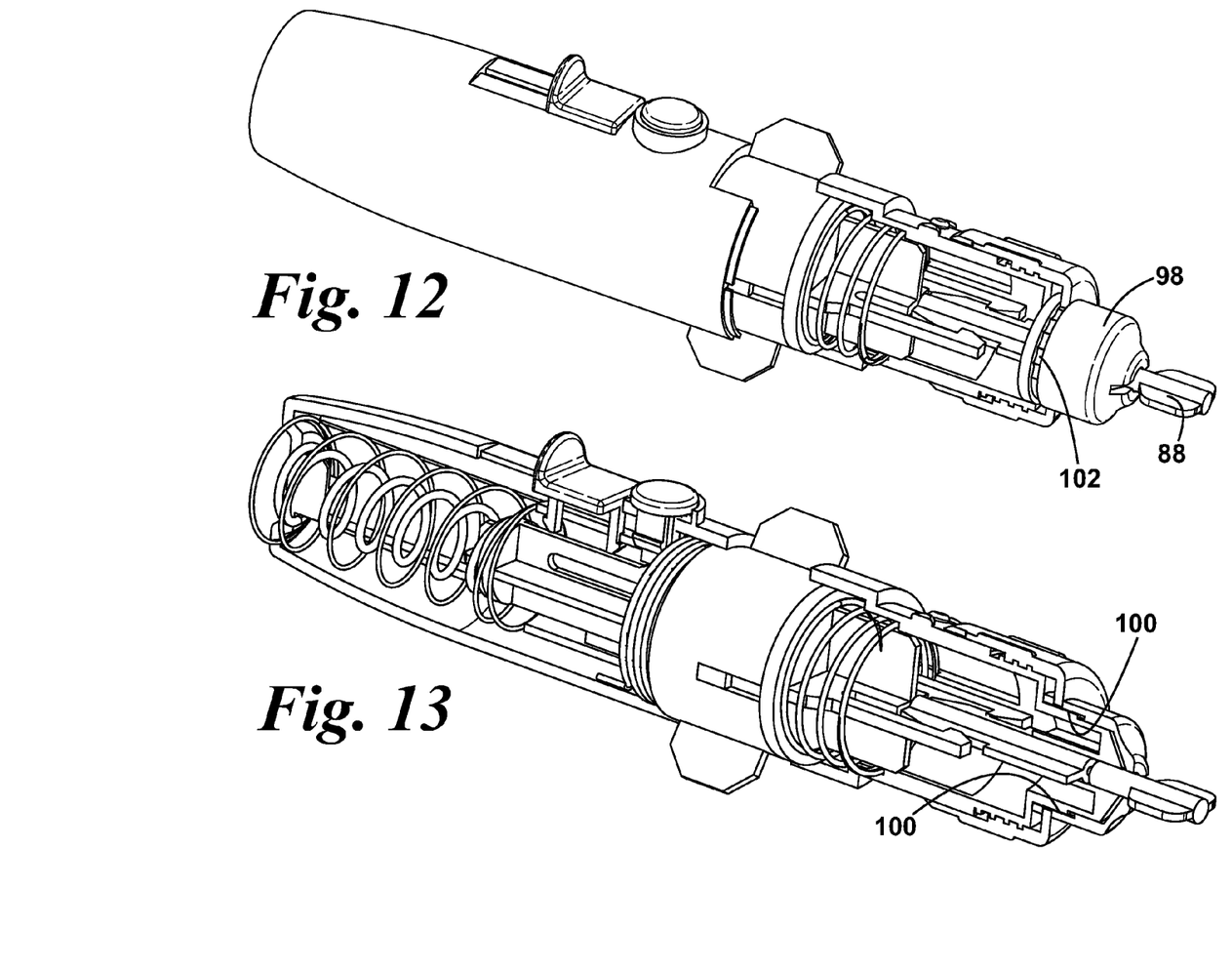
FIG. 12 is a view of the second embodiment of lancing device with the forward part thereof in section to illustrate the depth adjustment mechanism.
FIG. 13 is a full side section view of the second embodiment of lancing device.

In use, assuming the device already contains a used lancet, the nose portion 14 is unscrewed from the front end of the device and the lancet release lever 20 twisted by pressing one of the flaps 48. The lancet is held against rotation by engagement with the passage 76 and so the barbed resilient arms 28 are twisted out of engagement with the lancet so the lancet is released and can be dropped into a suitable disposal container (see FIGS. 4 and 5). The lancet release lever 48 is then allowed to return to its original position and a fresh lancet introduced into the device through the passage 76 so that it snaps into engagement with the resilient barbed arms of the lancet holder as seen in FIG. 6. The cap 88 of the lancet is then twisted off to uncover the tip, the tip still being safely within the device. The nose portion 14 is screwed on and the appropriate penetration depth set using the marker 90 and indicia 92. The device is cocked by sliding the cocking slider 16 rearwardly which pulls the hammer 58 backwards until the barb 62 latches against the latching surface 56 on the inner cylindrical portion 54. The user then offers the device up to their skin and presses the firing button 18 which pushes the barbed arm 60 inwards to unlatch it from the latching surface 56 so the hammer shoots forwardly and impacts the rear of the lancet holder 22 to drive the lancet holder and the lancet forwardly to project the lancet tip through the end of the housing and to rebound back into the housing.

Figures 14, 15, 16:
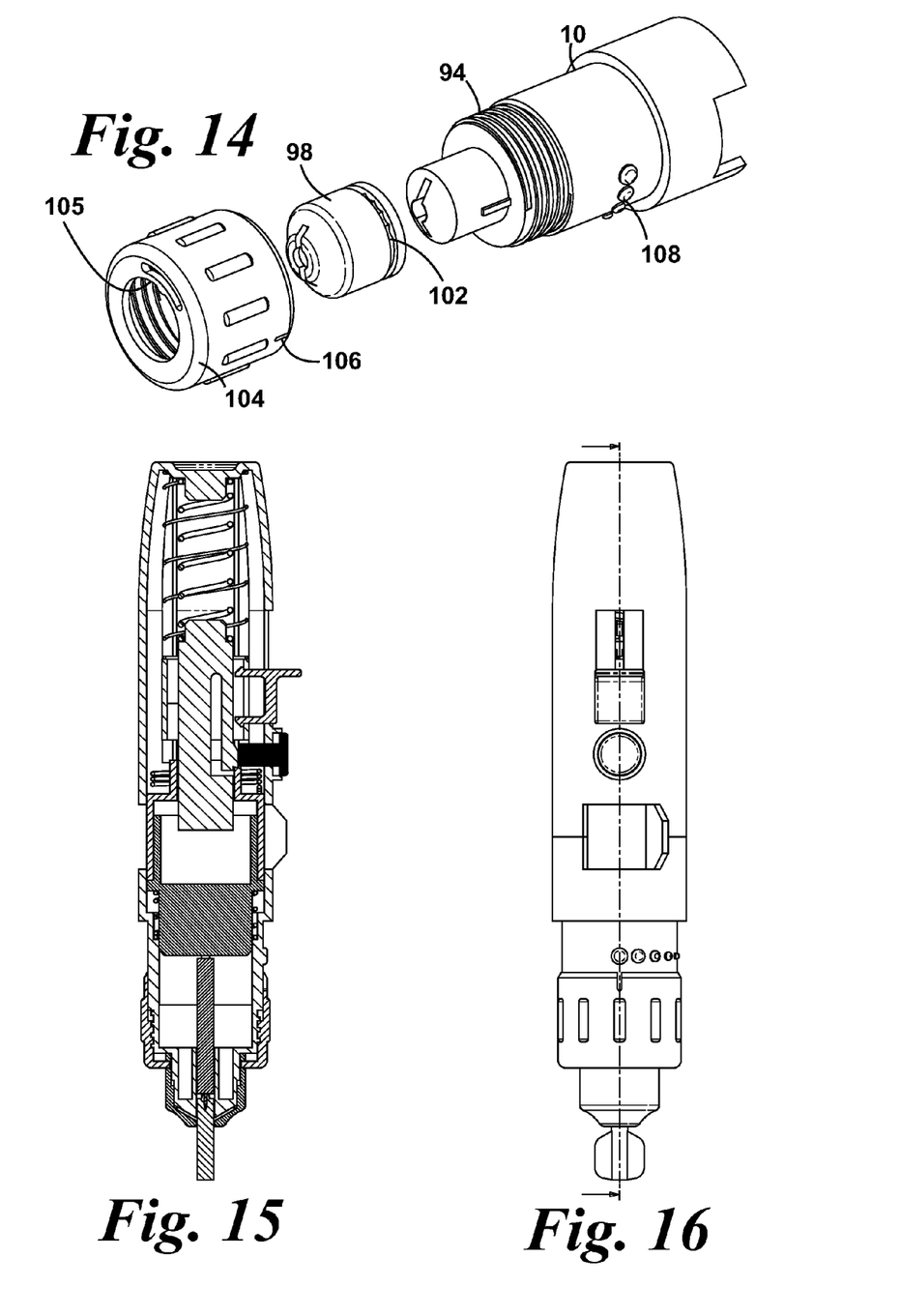
FIG. 14 is an exploded, detailed view of the depth adjustment device of the second embodiment.
FIG. 15 is a longitudinal cross-sectional view of the second embodiment.
FIG. 16 is a top plan view of the second embodiment.

Referring now to the second embodiment, in this arrangement the design of the nose portion has been changed so that it is not necessary to remove the nose portion in order to introduce a lancet into the device. Apart from the redesign of the nose portion, the construction and operation of the second embodiment is identical to that of the first and will not be described again. Referring in particular to FIG. 14, in this arrangement, the forward housing part 10 is provided with an external thread 94, and a forward extension of the front portion is provided with two diametrically opposed anti-rotation splines 96. The forward nose piece 98 is designed to slide onto the forward portion of the housing and has grooves 100 which slide over the splines 96 to prevent rotation. Captively mounted in a scalloped groove 102 is a nose collar 104 having an internal thread which is engageable with thread 94 on the housing. The collar 104 is formed with a resiliently mounted pip 105 which engages the scalloped region in the groove 102 on the nose piece 98 to provide a click detent action. When assembled, the nose piece 98 is held against rotation and turning the collar 104 adjusts the axial position of the nose piece 98. The collar has a marker 106 which indicates the penetration setting using indicia 108 on the forward housing. In use, a lancet can be introduced into the device before or after the depth setting has been adjusted.

The invention claimed is:

1. A lancing device, comprising:
   a housing adapted for receiving in use a replaceable lancet introduced into said housing, the housing having a threaded forward end;
   a drive provided in the housing, the drive being actuable to drive said lancet momentarily to project a tip of the lancet from the forward end of the housing; and
   a nose portion moveably mounted to the forward end of the housing and having an aperture through which said lancet projects when fired, said nose portion being threadedly engaged with the threaded forward end of said housing to allow a penetration depth of said lancet tip to be pre-set,
   wherein said nose portion is resiliently deformable between an undeformed position in which the nose portion is locked against rotation relative to the housing, and a deformed position in which the nose portion is free to rotate relative to the housing,
   wherein application of pressure to opposed external regions of said nose portion causes bodily deformation of the nose portion into the deformed position.

2. The lancing device according to claim 1, wherein said nose portion has a rearward skirt having at least one abutment disposed to face one or more complementary abutments on or associated with said housing, said skirt portion being resiliently bodily deformable between a position in which said abutments engage to prevent or resist rotary movement of said nose portion, and a position in which said abutments move away from each other to allow rotation.

3. The lancing device according to claim 2, wherein said rearward skirt is generally cylindrical.

4. The lancing device according to claim 1, wherein the housing comprises a forward housing part and a rearward housing part, and the nose portion is captive on the forward housing part.

5. The lancing device according to claim 4, wherein the forward housing part slideably receives a lancet holder which has a cylindrical rear portion to a forward end of which is a circumferential guide flange, and extending forwardly are two resiliently deformable arms terminating forwardly in inwardly directed barbs.

6. The lancing device according to claim 5, wherein the lancet holder is urged rearwardly by means of a compression spring acting between the circumferential guide flange and a rearwardly facing shoulder in the forward housing part.

7. The lancing device according to claim 5, wherein the resiliently deformable arms with their inwardly directed barbs are adapted to receive in one way snap arrangement a rear end of the lancet.

8. The lancing device according to claim 5, wherein the lancet has a main body portion having a central cylindrical stem and diametrically opposed flanges, and the flanges are chamfered at a rear end to assist engagement and snapping past the barbs.

9. The lancing device according to claim 5, wherein the lancet holder includes a thrust surface against which a rear end of the lancet rests.

10. The lancing device according to claim 1, wherein the device includes a cocking slider fired using a firing button, and the lancet is released using a lancet release lever.

11. The lancing device according to claim 1, wherein the opposed external regions of said nose portion are pressure pads.

12. The lancing device according to claim 11, wherein on pressing the pressure pads locking ribs are lifted away from engagement with splines so that nose portion can be rotated to adjust an axial position of a foremost portion of the nose portion and thus penetration depth.

13. A lancing device, comprising:
    a housing adapted for receiving in use a replaceable lancet introduced into said housing, the housing comprising a forward housing part and a rearward housing part;
    a drive actuable to drive said lancet momentarily to project a tip of the lancet from the housing; and
    a nose portion having an aperture through which said lancet projects when fired, said nose portion being threadedly engaged with a forward end of said housing to allow a penetration depth of said lancet tip to be pre-set, the nose portion being captive on the forward housing part,
    wherein said nose portion is resiliently deformable and an application of pressure to opposed external regions of said nose portion causes bodily deformation of the nose portion between a position in which the nose portion is locked against rotation and a position in which the nose portion is free to rotate,
    the forward housing part slideably receives a lancet holder which has a cylindrical rear portion to a forward end of which is a circumferential guide flange, and extending forwardly are two resiliently deformable arms terminating forwardly in inwardly directed barbs, and
    the cylindrical rear portion includes two diametrically opposed lugs which fit into respective slots formed in a cylindrical shell portion forming a part of a lancet release lever.

14. The lancing device according to claim 13, wherein the lancet release lever has protruding flaps which protrude forward through diametrically opposed slots formed between the forward and rearward housing parts.

15. The lancing device according to claim 13, wherein the lancet release lever is biased in a clockwise direction in frontal view by means of a torsion spring having a forward end engaged with a cylindrical shell and a rearward end on a set within the rearward housing part.

16. A lancing device, comprising:
    a housing adapted for receiving in use a replaceable lancet introduced into said housing, the housing comprising a forward housing part and a rearward housing part;
    a drive actuable to drive said lancet momentarily to project a tip of the lancet from the housing; and
    a nose portion having an aperture through which said lancet projects when fired, said nose portion being threadedly engaged with a forward end of said housing to allow a penetration depth of said lancet tip to be pre-set, the nose portion being captive on the forward housing part,
    wherein said nose portion is resiliently deformable and an application of pressure to opposed external regions of said nose portion causes bodily deformation of the nose portion between a position in which the nose portion is locked against rotation and a position in which the nose portion is free to rotate,
    the forward housing part slideably receives a lancet holder which has a cylindrical rear portion to a forward end of which is a circumferential guide flange, and extending forwardly are two resiliently deformable arms terminating forwardly in inwardly directed barbs, and
    the cylindrical rear portion steps in rearwardly to provide an inner cylindrical portion which defines a cylindrical latching surface.

17. The lancing device according to claim 16, wherein a hammer is slideably received in the inner cylindrical portion and urged forwardly by a drive spring acting between the hammer and a rear end of the rearward housing part.

18. The lancing device according to claim 17, wherein the hammer is provided with a forwardly extending resiliently deformable arm having a barb for cooperating with the latching surface on the cylindrical portion to latch the hammer in a cocked position.

19. The lancing device according to claim 17, wherein surrounding the aft end of the hammer is a cylindrical cocking shell having two inwardly directed lugs which project to either side of a longitudinal ventral rib on the hammer.

20. The lancing device according to claim 17, wherein a rear end disc is provided at a rearward end of the hammer.

\* \* \* \* \*